(12) United States Patent
Egashira et al.

(10) Patent No.: US 7,304,040 B2
(45) Date of Patent: Dec. 4, 2007

(54) SUPPRESSION OF POST-TRANSPLANT ARTERIOSCLEROSIS

(75) Inventors: Kensuke Egashira, 3-5-2-2-101, Momochihama, Sawara-ku, Fukuoka-shi (JP) 814-0001; Akira Takeshita, Fukuoka (JP); Masataka Sata, Tokyo (JP)

(73) Assignee: Kensuke Egashira, Fukuoka-shi (JP)

( * ) Notice: Subject to any disclaimer, the term of this patent is extended or adjusted under 35 U.S.C. 154(b) by 0 days.

(21) Appl. No.: 10/493,070

(22) PCT Filed: Nov. 1, 2002

(86) PCT No.: PCT/JP02/11441

§ 371 (c)(1),
(2), (4) Date: Nov. 24, 2004

(87) PCT Pub. No.: WO03/037376

PCT Pub. Date: May 8, 2003

(65) Prior Publication Data

US 2005/0222019 A1    Oct. 6, 2005

(30) Foreign Application Priority Data

Nov. 2, 2001 (JP) .............................. 2001-337861

(51) Int. Cl.
*A61K 48/00* (2006.01)
(52) U.S. Cl. ...................................................... 514/44
(58) Field of Classification Search .................. 514/44
See application file for complete search history.

(56) References Cited

U.S. PATENT DOCUMENTS 5,399,346 A * 3/1995 Anderson et al. ......... 424/93.21
5,705,360 A * 1/1998 Rollins et al. ............. 435/69.1

FOREIGN PATENT DOCUMENTS

| JP | 5-276986 | 10/1993 |
| JP | 2002-284698 | 10/2002 |
| WO | 96/38559 | 12/1996 |

OTHER PUBLICATIONS

Juengst, BMJ Jun. 28, 2003;326(7404):1410-1.*
Zhang et al., J Biol Chem. Jun. 3, 1994;269(22):15918-24.*
Deonarain, Expert Opin. Ther. Pat, 8: 53-69, 1998.*
Chen et al, Transplant immunology, 9: 301-314, 2002.*
Romano, Drugs, News Perspect, 16(5): 267-276, 2003.*
Thomas et al, Immunological Reviews, 196: 161-175, 2003.*
Ogata et al, Cardiology, 101: 144-158, 2004.*
Akowuah, et al, Ann Thorac Surg, 76: 959-66, 2003.*
Teizo Yoshimura, et al., The Journal of Experimental Medicine, vol. 169, pp. 1449-1459 1989.
Kouji Matsushima, et al., The Journal of Experimental Medicine, vol. 169, pp. 1485-1490 1989.
Teizo Yoshimura, et al., FEBS Letters, vol. 244, No. 2, pp. 487-493 1989.
Israel F. Charo, et al., Proc. Natl. Acad. Sci. USA, vol. 91, pp. 2752-2756 1994.
Shinsuke Yamagami, et al., Biochemical and Biophysical Research Communications, vol. 202, No. 2, pp. 1156-1162 Jul. 29, 1994.
Teizo Yoshimura, et al., The Journal of Immunology, vol. 147, No. 7, pp. 2229-2233 Oct. 1, 1991.
Egashira, Kensuke et al., A novel anti-monocyte chemo-attractant protein-1 gene therapy for atherosclerosis, Japanese Circulation Journal, Mar. 1, 2001, vol. 65, Supplement 1-A, p. 254 (OJ453).
Forsythe, J.L., Graft function and other risk factors as predictors of cardiovascular disease outcome., Transplantation, Sep. 27, 2001, vol. 72, Issue 6 Suppl., S16-9 (abstract) MEDLINE [online]: Retrieved from STN, MEDLINE Accession No. 2001538553.
Zhang, Yu Jun et al., Structure/Activity Analysis of Human Monocyte Chemoattractant Protein-1 (MCP-1) by Mutagenesis, The Journal of Biological Chemistry, Jun. 3, 1994, vol. 269, No. 22, pp. 15918 to 15924.
Egashira, Kensuke et al., Anti-monocyte chemoattractant protein-1 gene therapy inhibits vascular remodeling in rats: blockade of MCP-1 activity after intramuscular transfer of a mutant gene inhibits vascular remodeling induced by chronic blockade of NO synthesis, The FASEB Journal, Oct. 2000, vol. 14, Issue 13, pp. 1974 to 1978.
Kirchengast, Michael et al., Endothelin-1 and Endothelin Receptor Antagonists in Cardiovascular Remodeling, Proceedings of the Society for Experimental Biology and Medicine, Sep. 1999, vol. 221, No. 4, pp. 312-325.
Mitsuaki Isobe et al., "Ishoku Shinkan Domyaku Koka no Shinten Kijo to Yobo—in situ RT-PCR-ho ni yoru Kaiseki to Secchaku Sogal ni yoru Chiryo Koka", Ono Medical Research Foundation, The 8th Annual Report 1996 Nendo, Aug. 31, 1997, pp. 67 to 76.

* cited by examiner

*Primary Examiner*—Deborah Crouch
*Assistant Examiner*—Magdalene Sgagias
(74) *Attorney, Agent, or Firm*—Oblon, Spivak, McClelland, Maier & Neustadt, P.C.

(57) ABSTRACT

A preventive and/or therapeutic agent for post-transplant arteriosclerosis occurring as a rejection response to organ transplantation or for auto- or allo-arteriovenous graft post-transplant intimal thickening, wherein the agent contains, as an active ingredient, a monocyte chemoattractant protein-1 (MCP-1) function inhibitor. Administration of the MCP-1 function inhibitor enables prevention and treatment of post-transplant arteriosclerosis occurring as a rejection response to organ transplantation or for auto- or allo-arteriovenous graft post-transplant intimal thickening.

12 Claims, No Drawings

SUPPRESSION OF POST-TRANSPLANT ARTERIOSCLEROSIS

CROSS-REFERENCE TO A RELATED APPLICATION

The present application is a National Stage (371) of International Application PCT/JP02/11441, filed on Nov. 1, 2002, which claims priority to Japanese Patent Application No. JP 2001-337861, filed on Nov. 2, 2001.

TECHNICAL FIELD

The present invention relates to a preventive and/or therapeutic agent for post-transplant arteriosclerosis occurring as a rejection response to organ transplantation or for auto- or allo-arteriovenous graft post-transplant intimal thickening, and to a preventive and/or therapeutic method for post-transplant arteriosclerosis occurring as a rejection response to organ transplantation or for auto- or allo-arteriovenous graft post-transplant intimal thickening.

BACKGROUND ART

Implantation of an organ (e.g., the heart, a kidney, or a blood vessel) is often followed by a post-transplant rejection response. In an early stage of such a response, inflammation occurs in blood vessels in the transplanted organ, and in a later stage, arteriosclerosis lesions (intimal thickening) are formed. The post-transplant arteriosclerosis event is critical in clinical settings, as it leads to dysfunction of the transplanted organ and a lowered chance of successful engraftment. Although a variety of immunosuppressors have been used for management and prevention of such rejection responses, effects are not necessarily sufficient and not a few side effects result. Thus, a demand continues to exist for development of a new therapeutic method which takes into consideration the onset mechanism of the pathological conditions (Transplantation 72 (6 Suppl.): S16-9, 2001). Likewise, similar inflammatory changes are considered to participate in the intimal thickening occurring after transplantation of an auto- or allo-arteriovenous graft.

Recent research in the field of vascular biology has suggested that inflammation may be a common factor in the pathogenesis of these intractable pathological conditions (N. Engl. J. Med. 340, 115-126, 1999). Leukocytes have a function of disposal of foreign matter that has invaded the living body from the outside, and when the tissue is damaged, they come to concentrate at the damaged site, to thereby function to restore the tissue. The inflammation response is recognized as a situation where leukocytes exert their self-defense function excessively to damage the autologous tissue. For example, a coronary arteriosclerosis event occurring after heart transplantation is considered to be caused by inflammation evoked as an excessive self-defense response. This type of arteriosclerosis has an onset mechanism that clearly differs from that of ordinary arteriosclerosis, which involves infiltration of lipids and phagocytosis by macrophages on the lipids to form foamy cells.

An object of the present invention is to provide means for preventing the onset of post-transplant arteriosclerosis or post-transplant intimal thickening by preventing infiltration/accumulation of leukocytes which may otherwise occur in the implanted arteries when organ transplantation is performed.

Chemokines are a family of proteins exhibiting chemotactic activity toward leukocytes or lymphocytes. Chemokines are generally divided into four groups in terms of structure, and those having a molecular structure in which the first and second cysteines are aligned side by side are called CC chemokines.

Monocyte chemoattractant protein-1 (MCP-1), one of such CC chemokines, has itself been reported as a protein, and its cDNA sequence was elucidated at almost the same time (J. Exp. Med. 169, 1449-1459, 1989; J. Exp. Med. 169, 1485-1490, 1989; FEBS lett, 244, 487-493, 1989).

Receptors that recognize MCP-1 have been identified, and cDNA of each receptor has also been cloned (Proc. Natl. Acad. Sci. USA, 91, 2752-2756, 1994; Biochem. Biophys. Res. Commun. 202, 1156-1162, 1994). Currently, 11 CC chemokine receptors are known, and among them, an MCP-1 receptor is called CCR2.

Rollins et al. engineered amino acid mutants of the MCP-1 protein, and reported that some of them do not exhibit chemotactic activity (J. Bio. Chem. 269, 15918-15924, 1994). Of such mutants, a mutant named 7ND-MCP-1, in which amino acids 2 to 8 as counted from the N-terminus have been deleted, exhibited no chemotactic ability, although the mutant maintained the ability to bind itself to CCR2, or 7ND-MCP-1 functioned as a dominant negative to form a dimer with wild-type MCP-1, impeding the functions of MCP-1. As has also been known, a deletion occurring at the N-terminus of a chemokine can provide a strong dominant negative inhibitor against interaction with a chemokine receptor, through formation of hetero-dimers with corresponding intrinsic monomers of the chemokine, and that the inhibitor is useful for the treatment of articular rheumatism, inflammatory intestinal disease, multiple sclerosis, chronic pneumonia such as pulmonary fibrosis, and autoimmune diseases among other diseases (Japanese Kohyo (PCT) Patent Publication No. 11-506005).

Accordingly, the present invention provides a preventive and/or therapeutic agent for post-transplant arteriosclerosis occurring as a rejection response to organ transplantation or for auto- or allo-arteriovenous graft post-transplant intimal thickening, and also provides a preventive and/or therapeutic method for post-transplant arteriosclerosis occurring as a rejection response to organ transplantation or for auto- or allo-arteriovenous graft post-transplant intimal thickening.

DISCLOSURE OF THE INVENTION

The present inventors intramuscularly injected an expression vector (pcDNA3) containing a 7ND-MCP-1 gene to a model animal (mouse) at the thigh, and confirmed that 7ND-MCP-1 protein produced in the vector-plasmid-introduced muscle cells significantly suppressed the development of arteriosclerosis (intimal thickening) in an implanted heart. From this, the inventors have determined that an MCP-1 function inhibitor is useful as a preventive and/or therapeutic agent for post-transplant arteriosclerosis or auto- or allo-arteriovenous graft post-transplant intimal thickening, leading to completion of the invention.

Accordingly, the present invention provides a preventive and/or therapeutic agent for post-transplant arteriosclerosis or for auto- or allo-arteriovenous graft post-transplant intimal thickening, which agent contains, as an active ingredient, an MCP-1 function inhibitor.

The present invention also provides use of an MCP-1 function inhibitor in the manufacture of a preventive and/or therapeutic agent for post-transplant arteriosclerosis occurring as a rejection response to organ transplantation or for auto- or allo-arteriovenous graft post-transplant intimal thickening.

The present invention also provides a preventive and/or therapeutic method for post-transplant arteriosclerosis occurring as a rejection response to organ transplantation or for auto- or allo-arteriovenous graft post-transplant intimal thickening, characterized by administering, to a subject in need thereof, an effective amount of an MCP-1 function inhibitor.

BEST MODE FOR CARRYING OUT THE INVENTION

No particular limitations are imposed on the MCP-1 function inhibitor according to the present invention, so long as it can inhibit functions of MCP-1 in the living body. Specific examples of the MCP-1 function inhibitor include anti-MCP-1 antibodies (polyclonal or monoclonal), MCP-1 antagonists (including proteins and nonprotein low molecular compounds), and MCP-1 dominant negatives (including proteins and nonprotein low molecular compounds), and, in the case where the MCP-1 function inhibitor is a protein, a gene coding therefor may also considered to be the MCP-1 function inhibitor of the present invention. A variety of antibodies, antagonists, dominant negatives, and genes coding therefor which fall within the definition of the MCP-1 function inhibitor of the present invention have already been known, and, in addition, those which can be obtained through any known technique may be used in the present invention.

For example, an anti-MCP-1 antibody may be obtained through the method described in J. Immunology, 147, 2229-2233, 1991, and an MCP-1 antagonist and an MCP-1 dominant negative are known from, for example, Japanese Kohyo (PCT) Patent Publication No. 11-506005.

In the present invention, transfer of a gene coding for an MCP-1 function inhibitor is preferred over administration of a protein serving as an MCP-1 function inhibitor to the living body, in view that the gene can remain in the living body (blood) for a prolonged period of time.

In the present invention, use of an MCP-1 antagonist or an MCP-1 dominant negative, inter alia, use of 7ND-MCP-1, is preferred. Furthermore, genes coding for an MCP-1 antagonist or an MCP-1 dominant negative are preferred, with a gene coding for 7ND-MCP-1 being more preferred. As a gene coding for 7ND-MCP-1, DNA having a nucleotide sequence of SEQ ID NO: 1 is employed. This DNA can be engineered through a genetic engineering technique known per se. Briefly, the DNA can be created through PCR employing synthetic primers and the nucleotide sequence of DNA coding for a wild-type MCP-1 of SEQ ID NO: 2.

No particular limitations are imposed on the expression vector to be used for inducing expression of the gene in the living body, so long as the vector attains its assigned functions. Examples of useful vectors include plasmid vectors such as pcDNA3, pEF-BOS, and pXT1, and retrovirus vectors such as adenovirus and Sendai virus. When an expression vector is constructed, a promoter or an enhancer may be used, and in this case, no particular limitation is imposed on the promoter or the enhancer, so long as it functions in the host (living body). Examples of the promoter include, but are not limited to, SV40 promoter, CMV promoter, HSV-TK, SRα, and RSV.

In order to cause a gene to be expressed in the host (living body), use of a liposome may be another choice. In this case, the gene may be present inside the liposome, inside the lipid bilayer membrane that constitutes the liposome, or outside the membrane. A diversity of liposome compositions have been known to have the ability to express a gene in the host (living body).

In order to confirm that the 7ND-MCP-1 gene in fact produces 7ND-MCP-1 protein, ELISA assay may be performed to detect the protein in serum.

Indications of the drugs of the present invention include post-transplant arteriosclerosis (intimal thickening) occurring as a rejection response to organ transplantation and auto- or allo-arteriovenous graft post-transplant intimal thickening.

The MCP-1 function inhibitor, which is an active ingredient of the preventive and/or therapeutic agent for post-transplant arteriosclerosis or auto- or allo-arteriovenous graft post-transplant intimal thickening, is administered to the living body orally or parenterally. When the MCP-1 function inhibitor is a protein, parenteral administration is preferred. Examples of the parenteral administration include injection, and no particular limitations are imposed on the injection route. For example, intra-arterial, intravenous, intramuscular, transdermal, or subcutaneous injection may be performed at any site other than the implanted organ or the graft. When the MCP-1 function inhibitor is administered through injection, the product form may be a liquid for injection, which can be produced through a known drug production technique. In the manufacture of injection products, known additives may be used, including, for example, an isotonicity agent, a buffer, a preservative, a vehicle, and a soothing agent. The dosage may be determined in consideration of the patient's condition, age, sex, body weight, etc. The dose may be 0.1 to 1,000 mg in the case of a protein, or 0.01 to 100 mg in the case of a gene, and in either case, the dose may be administered once every 2 to 4 weeks.

EXAMPLES

The present invention will next be described in more detail by way of examples, which should not be construed as limiting the invention thereto.

(1) Construction and Expression of 7ND-MCP-1

A vector plasmid coding for 7ND-MCP-1 was constructed through recombinant PCR using, as a template, pcDNA3 vector plasmid encoding MCP-1. The presence of all mutations was confirmed by the DNA sequence analysis performed in both directions. The resultant PCR product coding for 7ND-MCP-1 was integrated into the pcDNA3 vector plasmid at a multi-cloning site, followed by transformation into E. coli. Plasmid DNA was purified by use of a Plasmid Giga Kit (product of Qiagen).

(2) Mouse Model of Ectopic Heart Implantation

Each animal of a group of male B10.D2 mice (6 weeks old) was given, at the right and left thigh muscles, 50 μg of 7ND-MCP-1 gene/pcDNA3 (n=9; hereinafter referred to as "7ND treatment group") or, in a control, 50 μg of Green Flourescent Protein gene/pcDNA3 (n=9; hereinafter referred as "control group") by way of intramuscular injection (right: 25 μg/25 μl Tris/EDTA buffer, left: 25 μg/25 μl Tris/EDTA buffer). Immediately thereafter, a voltage of 100V was applied six times in accordance with the method described by Aihara & Miyazaki (Nature Biotech vol. 16, 867-870. 1998).

On day 3 following the gene transfer, the heart of a 6-week-old male DBA2 mouse was transplanted into the abdominal cavity of the B10.D2 mouse in accordance with the method described by Furukawa et al. (Circulation, 1996, 93, 333-339). Briefly, the heart was removed from the DBA2 mouse and immediately thereafter, abdominal arteriovenous anastomosis was performed in the B10.D2 mouse, whereby the heart implant surgery was complete. Eight weeks after the surgery, the implanted heart was taken out and fixed with formalin. The specimen was embedded in paraffin. Five slices, cut at intervals of 500 μm, were prepared from each heart sample. The slices were stained with hematoxin-eosin, and morphological measurement was performed for each of randomly selected 10 coronary arterial cross sections.

(3) Results

The ratio of newly developed intima/media was found to be 0.84/0.07 in the control group, whereas the ratio was 0.54/0.09 in the 7ND treatment group, showing that new formation of the intima was significantly suppressed in the 7ND treatment group as compared with the control group.

Thus, the test has clarified that administration of an MCP-1 function inhibitor is effective for prevention and/or therapy of post-transplant arteriosclerosis or auto- or allo-arteriovenous graft post-transplant intimal thickening. The action mechanism is considered to be attributed to the effect of preventing recipient's inflammatory cells from infiltrating into or adhering to blood vessels of the graft.

INDUSTRIAL APPLICABILITY

The MCP-1 function inhibitor is useful as a preventive and/or therapeutic agent for post-transplant arteriosclerosis occurring as a rejection response to organ transplantation or for auto- or allo-arteriovenous graft post-transplant intimal thickening. The inhibitor is also useful when employed in the preventive and/or therapeutic method for post-transplant arteriosclerosis occurring as a rejection response to organ transplantation or in the method for auto- or allo-arteriovenous graft post-transplant intimal thickening.

The invention claimed is:

1. A method for suppressing post-transplant arteriosclerosis comprising: intramuscularly administering a polynucleotide that encodes 7ND-MCP-1 operably linked to a promoter to an organ or tissue transplant subject, wherein expression of said polynucleotide suppresses the formation of intimal thickening in the transplanted organ or tissue.

2. The method of claim 1, wherein said polynucleotide comprises SEQ ID NO: 1.

3. The method of claim 1, wherein said subject has undergone organ transplantation.

4. The method of claim 1, wherein said subject has received an allograft.

5. The method of claim 1, wherein said subject has received an autograft.

6. The method of claim 1, wherein said subject has undergone auto-arteriovenous grafting.

7. The method of claim 1, wherein said subject has undergone allo-arteriovenous grafting.

8. The method of claim 1, wherein said polynucleotide is administered in an expression vector.

9. The method of claim 1, wherein said polynucleotide is administered in a liposome.

10. The method according to claim 1, wherein the polynucleotide is intramuscularly administered to a site other than an implanted organ or a graft.

11. The method of claim 1, wherein said polynucleotide is administered prior to a transplant.

12. The method of claim 1, wherein said polynucleotide is administered after a transplant.

* * * * *

SEQUENCE LISTING

```
<160> NUMBER OF SEQ ID NOS: 2

<210> SEQ ID NO 1
<211> LENGTH: 279
<212> TYPE: DNA
<213> ORGANISM: Homo sapiens

<400> SEQUENCE: 1
atgaaagtct ctgccgccct tctgtgcctg ctgctcatag cagccacctt cattccccaa      60
gggctcgctc aggtcacctg ctgttataac ttcaccaata ggaagatctc agtgcagagg     120
ctcgcgagct atagaagaat caccagcagc aagtgtccca aagaagctgt gatcttcaag     180
accattgtgg ccaaggagat ctgtgctgac cccaagcaga agtgggttca ggattccatg     240
gaccacctgg acaagcaaac ccaaactccg aagacttga                            279

<210> SEQ ID NO 2
<211> LENGTH: 300
<212> TYPE: DNA
<213> ORGANISM: Homo sapiens

<400> SEQUENCE: 2
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
```

```
aaagaagctg tgatcttcaa gaccattgtg gccaaggaga tctgtgctga ccccaagcag      240
aagtgggttc aggattccat ggaccacctg gacaagcaaa cccaaactcc gaagacttga      300
```